| United States Patent [19] | [11] Patent Number: 4,761,476 |
|---|---|
| Treybig | [45] Date of Patent: Aug. 2, 1988 |

[54] COMPOUNDS FORMED BY THE REACTION OF PIPERAZINE, AND DERIVATIVES THEREOF, WITH GLYOXAL, AND DERIVATIVES THEREOF

[75] Inventor: Duane S. Treybig, Lake Jackson, Tex.

[73] Assignee: The Dow Chemical Company, Midland, Mich.

[21] Appl. No.: 749,697

[22] Filed: Jun. 28, 1985

[51] Int. Cl.$^4$ .................. C07D 295/08; C07D 295/10
[52] U.S. Cl. .................................. 544/357; 544/386
[58] Field of Search ............................. 544/357, 386

[56] References Cited

U.S. PATENT DOCUMENTS

| 2,756,231 | 7/1956 | Back et al. | 544/357 |
|---|---|---|---|
| 2,969,365 | 1/1961 | Levis | 544/358 |
| 2,993,900 | 7/1961 | Biel | 544/360 |
| 2,995,544 | 8/1961 | Bourgeois | 526/339 |
| 3,036,076 | 5/1962 | Gabler | 544/357 |
| 3,565,837 | 2/1971 | Drawert | 544/357 |
| 4,013,787 | 3/1977 | Varlerberghe et al. | 544/357 |
| 4,041,038 | 8/1977 | Irikura | 544/391 |
| 4,094,687 | 6/1978 | Lawton | 106/21 |

FOREIGN PATENT DOCUMENTS

| 2623772 | 12/1976 | Fed. Rep. of Germany . | |
|---|---|---|---|
| 3244956 | 6/1984 | Fed. Rep. of Germany . | |
| 47997 | 12/1972 | Japan | 544/357 |
| 781528 | 8/1957 | United Kingdom | 544/357 |

OTHER PUBLICATIONS

Lawton, Chem. Abst. 90-144283a.
Biel, Chem. Abst. 55-3493i.
Lawton, Chem. Abst. 89-207282b.
Irikura, Chem. Abst. 86-89893q, eq. DE 2623772.
Diehr et al, Chem. Abst. 101-90779s.
Dara et al, Chem. Abst. 87-201470y.
Fuchs et al, Chem. Abst. 84-174805r.
Morishita et al., Chem. Abst., 89-122846p.
Kafka et al., Chem. Abst., 104-88498t.
Foerster et al., Chem. Abst. 95-7285s.
Baba et al, Chem. Abst. 92-15170d.
Barrows; Chem. Abst. 95-209706r.
Sugiyama et al, CA 74-124480d.
Currie et al, CA66-85759q.
Dinwoodie et al, CA66-85760h.

*Primary Examiner*—Robert Gerstl
*Assistant Examiner*—Cecilia Shen

[57] ABSTRACT

The reaction products of piperazine or alkyl, aryl or aralkyl substituted piperazine and glyoxal or alkyl substituted glyoxal.

8 Claims, No Drawings

COMPOUNDS FORMED BY THE REACTION OF PIPERAZINE, AND DERIVATIVES THEREOF, WITH GLYOXAL, AND DERIVATIVES THEREOF

BACKGROUND OF THE INVENTION

I. Field of the Invention

This invention relates to the reaction products of piperazine or alkyl, aryl or aralkyl substituted piperazine with glyoxal or alkyl substituted glyoxal.

II. Description of the Prior Art

In the article titled "Glyoxal Derivatives. III. The Reaction of Glyoxal with some secondary Amines" by J. M. Kliegman and R. K. Barnes in *Journal of Heterocyclic Chemistry*, Vol. 7, October 1970, pp 1153–1155, the reaction of piperidine and glyoxal is disclosed.

The reaction of a vicinal glycol and piperazine according to U.S. Pat. No. 2,969,365 forms an addition compound.

U.S. Pat. Nos. 4,094,687; 2,995,544; and 2,993,900 each relate to reaction products of piperazine.

SUMMARY OF THE INVENTION

The present invention is directed to the reaction compounds of piperazine or an alkyl, aryl or aralkyl substituted piperazine with glyoxal or alkyl substituted glyoxal. In its most specific aspects the present invention is directed to the new compositions of matter 1,2-bis(piperazinyl)ethanediol and 2-hydroxy-1-(1-piperazinyl)ethanone.

DETAILED DESCRIPTION

The compositions of matter of the present invention are the reaction products of a piperazine having the following general formula:

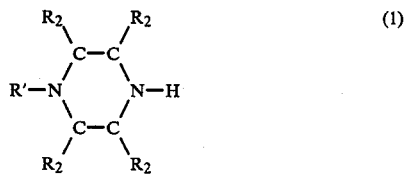

where
R is hydrogen; $C_1$ to $C_{10}$ alkyl, preferably $C_1$ to $C_4$ alkyl; aryl or aralkyl; and
R' is hydrogen; $C_1$ to $C_{20}$ alkyl or alkyl with hydroxy substituents; aryl or aralkyl with glyoxal(ethanedial) or alkyl substituted glyoxal having the following formula:

where R" is hydrogen or $C_1$ to $C_4$ alkyl.

The preferred reactants are piperazine and glyoxal, however the piperazines substituted by alkyl groups at the 1,2,3,5 and 6 positions are reactants for forming the compositions of the present invention. Such piperazines are 1-methylpiperazine; 2-methylpiperazine; 2,3-dimethylpiperazine; 2,5-dimethylpiperazine; 2,6-dimethylpiperazine; 1,2-dimethylpiperazine; 1,4-dimethylpiperazine; 1-ethylpiperazine; 2-ethylpiperazine; 2,3-diethylpiperazine; 2,5-diethylpiperazine; 2,6-diethylpiperazine; 1-propylpiperazine; 2-propylpiperazine; 1-ethyl-3-methylpiperazine; 1-butylpiperazine; 2-butylpiperazine; 1-dodecyl-1-piperazine; 1-octadecyl-1-piperazine; 1-piperazine ethanol [1-(2-hydroxyethyl)piperazine]; 1-piperazine propanol; 3-piperazino-1,2-propanediol; 1-phenylpiperazine (the method of making being disclosed in Chemical Abstracts 56: 10137 B); 2-phenylpiperazine; 2-ethyl-1-phenylpiperazine 2,3,5,6-tetraphenylpiperazine, (the method of making being disclosed in Chemical Abstracts 74: 124480 D); mixtures thereof and the like.

Glyoxal dihydrate, 40% aqueous solution of glyoxal, glyoxal hydrogen sulfite and 2,3-dihydroxy-1,4-dioxane are glyoxal equivalents. Glyoxal is liberated from glyoxal hydrogen sulfite with a base. Reactions with 2,3-dihydroxy-1,4-dioxane gives ethylene glycol as the sole by-product. Pyruvaldehyde(methylglyoxal); 2,3-butanedione(dimethylglyoxal) and 2,3-pentanedione(ethylmethylglyoxal) can be substituted for glyoxal.

The reaction of the piperazines and glyoxal is carried out utilizing 0.5 mole to ten moles of the piperazine to each mole of glyoxal. The reaction products are the corresponding ethanone and ethanediol. If the corresponding ethanone is desired, the mole ratio of piperazine to glyoxal is preferably 0.5:1. On the other hand, to form the corresponding ethanediol, preferably two or more moles of the piperazine to each mole of glyoxal is used. If the substituted piperazine is liquid, the reaction is carried out by adding the glyoxal or alkyl substituted glyoxal in a solvent, which may be water or an alcohol. When piperazine is used, it is first dissolved in a solvent which may be water or an alcohol but preferably is an alcohol such as methanol. Other suitable solvents such as ethers or other hydrocarbons which dissolve the reactants may be used. Preferably the reaction is carried out by maintaining the piperazine either with no solvent or in a solvent such as an alcohol at a temperature between 0° C. and 150° C., preferably between 0° and 75° C. To the liquid piperazine or substituted piperazine is added glyoxal or substituted glyoxal while maintaining good mixing which results in the reaction products of the present invention precipitating as a mixture. The reaction is illustrated by the following general equation:

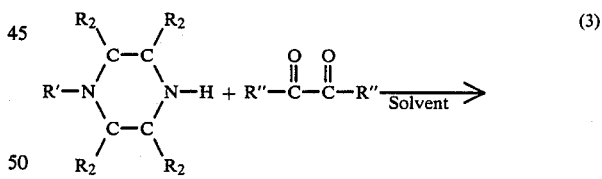

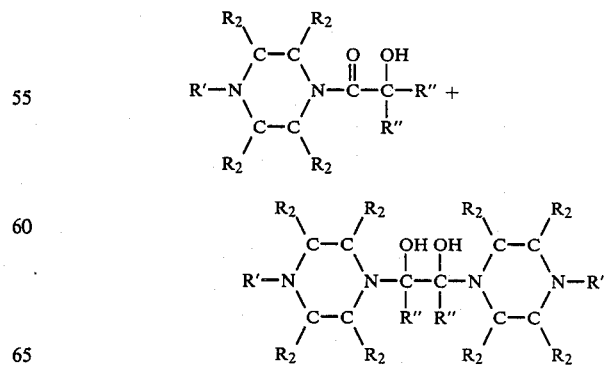

These new compositions of matter are useful as hydrochloric acid corrosion inhibitors. Further, the diol compounds may have utility as a lubricant initiators, and the ethanone compounds may be used as epoxy resin hardeners, when R' is hydrogen or a hydroxy substituted alkyl.

The present invention may also be further illustrated by the following specific examples:

EXAMPLE I

To a two liter kettle equipped with a reflux condenser, addition flask, immersion thermometer, mechanical stirrer and nitrogen purge system was added 515.8 g (6 moles) piperazine dissolved in 600 ml water. The contents in the resin kettle were stirred under nitrogen at 35° C. 218 g of 40 wt% glyoxal (1.5 moles) in water were diluted further with 70 g of water and added dropwise to the reactor contents over a period of twenty minutes. The reactor contents were allowed to stir at ambient temperature for thirty minutes. The reactor mixture became yellow and cloudy. A white crystalline solid was deposited on the kettle walls. The white crystalline solid was identified as piperazine hydrate by infrared spectrometry. The reactor mixture was filtered using a sintered funnel of medium porosity by vacuum. A tan colored solid was recovered. On washing with ethanol, the tan colored solid became a white solid. Infrared spectroscopy of the white solid showed no evidence of carbonyl groups but the presence of hydroxyl groups. Electron impact and chemical ionization mass spectrometry indicated the white solid was 1,2-bis(piperazinyl)ethanediol:

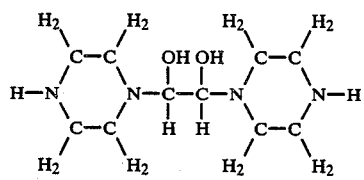

(4)

The white solid was found to contain 56.3% carbon, 8.88% hydrogen, 22.1% nitrogen and 12.72% oxygen by CHN analysis. The percent carbon, hydrogen, nitrogen and oxygen calculated from the molecular formula of 1,2-bis(piperazinyl)ethanediol is 52.2, 9.6, 24.3 and 13.9%, respectively. The percent yield for 1,2-bis(piperazinyl)ethanediol was 23.3%. The filtrate was transferred to a liter round bottom flask and water removed by rotary evaporation. A brown oily water soluble liquid remained after the rotary evaporation. Infrared spectroscopy showed the brown oil liquid consisted of piperazine hydrate, a compound containing an amide group (1645 cm$^{-1}$) and 1,2-bis(piperazinyl)ethanediol. Electron impact ionization mass spectroscopy indicated the compound containing the amide group was 2-hydroxy-1-(1-piperazinyl)ethanone:

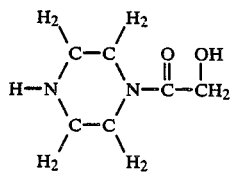

(5)

EXAMPLE II

To a two liter kettle equipped with a reflux condenser, addition flask, immersion thermometer, mechanical stirrer and nitrogen purge system was added 257.6 g (3.0 moles) piperazine dissolved in 1300 ml methanol. The apparatus was cooled with an ice bath to 0° to 5° C. 216 g of 40 wt% glyoxal (1.5 moles) in water was added dropwise to the reactor contents over a period of forty-three minutes. The reactor contents were a yellow milky color. A white solid was recovered from the reactor mixture by filtration using a 600 ml pyrex sintered funnel of medium porosity by vacuum. The white solid was washed with benzene, ethanol and benzene and dried under vacuum at 100° C. Electron impact and chemical ionization mass spectrometry indicated the white solid was 1,2-bis(piperazinyl)ethanediol. The white solid was found to contain 54.7% carbon, 22.8% nitrogen, 9.09% hydrogen, 13.21% oxygen, 10.6% tertiary nitrogen and 11.7% secondary nitrogen. The percent carbon, nitrogen, hydrogen, oxygen, tertiary nitrogen and secondary nitrogen calculated from the molecular formula of 1,2-bis(piperazinyl)ethanediol is 52.2, 24.3, 9.6, 13.9, 12.1 and 12.1%, respectively. Bis(1,2-piperazinyl)ethanediol was observed to melt between 190°–208° C. The melted bis(1,2-piperazinyl)ethanediol was a reddish brown liquid. The percent yield for bis(1,2-piperazinyl)ethanediol was 31.97%.

The foregoing example illustrates a preferred method for the preparation of the compounds of the present invention. The use of the alcohol eliminates the piperazine hydrate, which is formed when water is used as the solvent, and thus makes the separation of the compounds easier.

The utility of the compositions of the present invention are illustrated by the following example:

EXAMPLE III 1,2-bis(piperazinyl)ethanediol and an aqueous solution containing 1,2-bis(piperazinyl)ethanediol, 2-hydroxy-1-(1-piperazinyl)ethanone and piperazine hydrate were evaluated as corrosion inhibitors in acid and gas conditioning applications.

In the acid corrosion inhibition study, a test tube containing 0.2% of the inhibitor, a carbon steel coupon and 10% hydrochloric acid were heated in a one liter Parr bomb for 6 hours at 80° C. 1,2-bis(piperazinyl)ethanediol and the aqueous solution containing 1,2-bis(piperazinyl)ethanediol, 2-hydroxyl-1-(1-piperazinyl)ethanone and piperazine hydrate exhibited 67% and 55% corrosion inhibition, respectively.

In the gas conditioning corrosion inhibition study, a test tube containing 0.2% of the inhibitor, a mild steel coupon and 25 milliliters of 30% aqueous monoethanolamine saturated with carbon dioxide was heated in a 1 liter Parr bomb at 140° C. for 20.5 hours. 1,2-Bis(piperazinyl)ethanediol and the aqueous solution containing the products from the reaction of piperazine and glyoxal exhibited 26% and 25% corrosion inhibition, respectively.

While the invention has been described herein with reference to certain specific materials, procedures and examples, it is understood that the invention is not restricted to the particular materials, combination of materials and procedures selected for the purpose of illustration. Numerous variations of such details can be employed by those skilled in the art within the scope of this invention which is defined by the appended claims.

I claim:

1. A composition of matter having the following chemical formula:

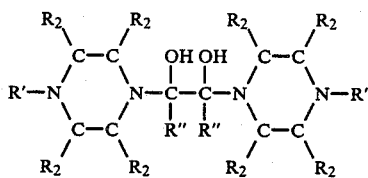

where
R and R' are hydrogens; and
R" is hydrogen or $C_1$ to $C_4$ alkyl.

2. The composition which results from reacting

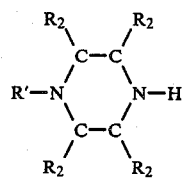 (A)

where R and R' are hydrogens; with

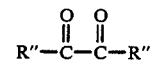 (B)

where R" is hydrogen or $C_1$ to $C_4$ alkyl, wherein components (A) and (B) are employed in quantities which provide a mole ratio of (A):(B) of from about 0.5:1 to about 10:1.

3. A composition of claim 2 wherein the mole ratio of (A):(B) is from about 1:1 to about 4:1.

4. A composition of claim 2 wherein the mole ratio of (A):(B) is from about 1:1 to about 2:1.

5. A composition of claim 2 or 3 where component (A) is piperazine and component (B) is glyoxal.

6. A composition formed from the reaction of 2 molecules of piperazine with 1 molecule of glyoxal.

7. A composition where the compound is formed from the reaction of 1 molecule of piperazine with 1 molecule of glyoxal.

8. A diol product formed from the reaction of 2 molecules of piperazine with 1 molecule of glyoxal.

* * * * *